United States Patent [19]

Watabe et al.

[11] Patent Number: 4,825,158

[45] Date of Patent: Apr. 25, 1989

[54] METHOD OF DETECTING CONDUCTIVE MATERIAL CONTAINED IN GLASS FIBER BY DETECTING CHANGES IN AMPLITUDE AND FREQUENCY OF AN OSCILLATOR AND DETECTING APPARATUS THEREFOR

[75] Inventors: Kenzo Watabe; Mitsuo Yabuki; Kazuyuki Iwama; Toshihiko Yokoi, all of Koriyama, Japan

[73] Assignee: Nitto Glass Fiber Mfg. Co., Ltd., Fukushima, Japan

[21] Appl. No.: 63,266

[22] Filed: Jun. 17, 1987

[30] Foreign Application Priority Data

Jun. 20, 1986 [JP] Japan ............................ 61-142729

[51] Int. Cl.$^4$ ...................... G01N 27/82; G08B 21/00
[52] U.S. Cl. ..................................... 324/237; 331/65; 340/677
[58] Field of Search ............... 324/207, 236, 237, 327, 324/328, 61 R; 340/675–677; 73/159, 160; 361/180; 331/65

[56] References Cited

U.S. PATENT DOCUMENTS

| | | | |
|---|---|---|---|
| 2,580,670 | 1/1952 | Gilbert | 324/236 |
| 3,737,764 | 6/1973 | Dufayet | 324/237 |
| 3,745,451 | 7/1973 | Goyette | 324/237 X |
| 3,974,442 | 8/1976 | Savidge et al. | 324/236 X |
| 4,004,216 | 1/1977 | Natens et al. | 324/233 |
| 4,286,261 | 8/1981 | Wagner et al. | 324/327 X |
| 4,473,799 | 9/1984 | Favre | 324/236 X |

FOREIGN PATENT DOCUMENTS 214748 12/1984 Japan .
20138 2/1985 Japan .

OTHER PUBLICATIONS

Ogren, V. G., Sensor Circuit Utilizing Variable Inductance Input, IBM Tech. Discl. Bull., vol. 14, No. 4, Sep. 1971, p. 1225.

*Primary Examiner*—Gerard R. Strecker
*Attorney, Agent, or Firm*—Henry Sternberg; Bert J. Lewen

[57] ABSTRACT

A method and apparatus for detecting conductive material contained in glass fiber, in which it is possible to detect fine conductive material contained in glass fiber under the condition that the glass fiber is running in the process of manufacturing the glass fiber, and in which it is possible to detect only the conductive material accurately without being affected by moisture or the like. The method and apparatus are arranged such that a state of oscillation is generated in advance by using an LC oscillator or the like disposed in the vicinity of a moving path of glass fiber in the manufacturing process so that a change may be caused in a reactance element in the oscillator by conductive material which may be contained in the glass fiber to thereby cause a change in the state of oscillation, the change in oscillation output being taken out as changed in amplitude and frequency by using an AM detector and an FM detector respectively, the taken-out AM and FM detection signals being combined with each other by a composite wave generator, the composite wave signal being compared with a reference level to thereby detect the conductive material maldistributed in the glass fiber.

11 Claims, 3 Drawing Sheets

METHOD OF DETECTING CONDUCTIVE MATERIAL CONTAINED IN GLASS FIBER BY DETECTING CHANGES IN AMPLITUDE AND FREQUENCY OF AN OSCILLATOR AND DETECTING APPARATUS THEREFOR

BACKGROUND OF THE INVENTION

1. Field of the Invention

The present invention relates to a method and an apparatus for detecting electrically-conductive material (hereinafter simply referred to as "conductive material") contained in glass fiber in a state of maldistribution, and relates to a method and an apparatus in which existence of fine conductive material which is possibly contained in glass fiber can be detected easily and accurately in the condition that the glass fiber is running in a manufacturing process of the glass fiber.

2. Description of the Related Art

Fine particles of conductive material may sometimes be contained in a state of maldistribution in glass fiber such as glass filaments, glass yarns or strands, or the like, constituting glass roving or glass cloth. This is because glass may contain metal components due to batch material, clay brick, or the like. The conductive material contained in glass fiber may cause a problem that electrical insulating properties are deteriorated when the glass fiber is applied to printed circuit substrates or the like. Accordingly, it is necessary to remove such a part of the glass fiber in which conductive material is contained, in the manufacturing process of the glass fiber.

As methods of detecting conductive material contained by a very small amount in glass fiber, conventionally known are a method which utilizes changes in dielectric constant, a method which utilizes a phase difference in a microwave, and a method which utilizes electric discharge. In the detection method utilizing changes in dielectric constant, it is necessary to directly measure the dielectric constant of glass fiber. In the detection method utilizing a phase difference in a microwave, conductive material or a fault in glass fiber is detected by a phase difference between a transmitting waveform and a receiving waveform of a microwave (JP-A No. 60-20138). In the detection method utilizing electric discharge, conductive material contained in glass fiber is detected by causing high-frequency discharge on the conductive material (JP-A No. 59-214748).

In the detection method utilizing changes in dielectric constant, there is such a problem that when the amount of conductive material contained in glass fiber is extremely small, the value of a dielectric constant to be measured is so small that a measuring instrument becomes insufficient to indicate the value of a measured dielectric constant so that measurement becomes impossible. Unless glass fiber is in a stationary state, generally, it is impossible to measure a dielectric constant, and therefore the detection method utilizing changes in dielectric constant cannot be applied to the case where glass fiber is moving. Accordingly, there is a problem that this method cannot be utilized at all in production management of glass fiber. In the detection method utilizing a phase difference in a microwave as well as in the detection method utilizing electric discharge, there is a disadvantage that the capability of detecting conductive material contained in glass fiber may be extremely lowered owing to an influence of a hiding action of moisture, size, dust, or the like, attached on the surfaces of the glass fiber. Granting that there is not such a hiding action due to those factors, among various kinds of conductive material contained in glass fiber, it has been impossible to detect those smaller than 2 mm in length in the axial direction of the glass fiber as a matter of fact.

SUMMARY OF THE INVENTION

It is an object of the present invention to provide a method and an apparatus for detecting conductive material contained in glass fiber, in which the conductive material can be detected even in the case where the glass fiber is moving in the process of manufacturing the glass fiber, in which only the conductive material maldistributed in the glass fiber can be detected without being affected by moisture, size, dust, or the like, attached on the surfaces of the glass fiber, and in which the conductive material can be detected even if it is a minute one having a length smaller than 2 mm in the axial direction of the fiber.

In order to achieve the above object, according to an aspect of the present invention, the method of detecting conductive material contained in glass fiber is arranged such that a state of oscillation is generated in advance by using an LC oscillator so as to make it possible to detect existence of conductive material maldistributed in glass fiber on the basis of a change in the state of oscillation caused by a change in reactance of a reactance element constituting the oscillator due to an action on the reactance element by the conductive material.

According to another aspect of the present invention, in order to realize the above method, the apparatus for detecting conductive material in glass fiber comprises a reactance element disposed in the vicinity of the glass fiber and having reactance which is changed by the conductive material in the glass fiber, an LC oscillator including the reactance element as a circuit component thereof, a first detector for AM detecting an output of the LC oscillator to thereby produce an AM detection signal, a second detector for FM detecting the output of the LC oscillator to thereby produce an FM detection signal, a composite wave generator for combining the AM and FM detection signals to thereby produce a composite signal, and a comparator for comparing the composite signal with a reference value to thereby produce a conductive material detection signal.

BRIEF DESCRIPTION OF THE DRAWINGS

Other objects, features and advantages of the present invention will be apparent more fully from the following description taking in conjunction with the accompanying drawings, wherein.

DESCRIPTION OF THE PREFERRED EMBODIMENT

An embodiment according to the present invention will be described hereunder with reference to the accompanying drawings.

Figure 1:
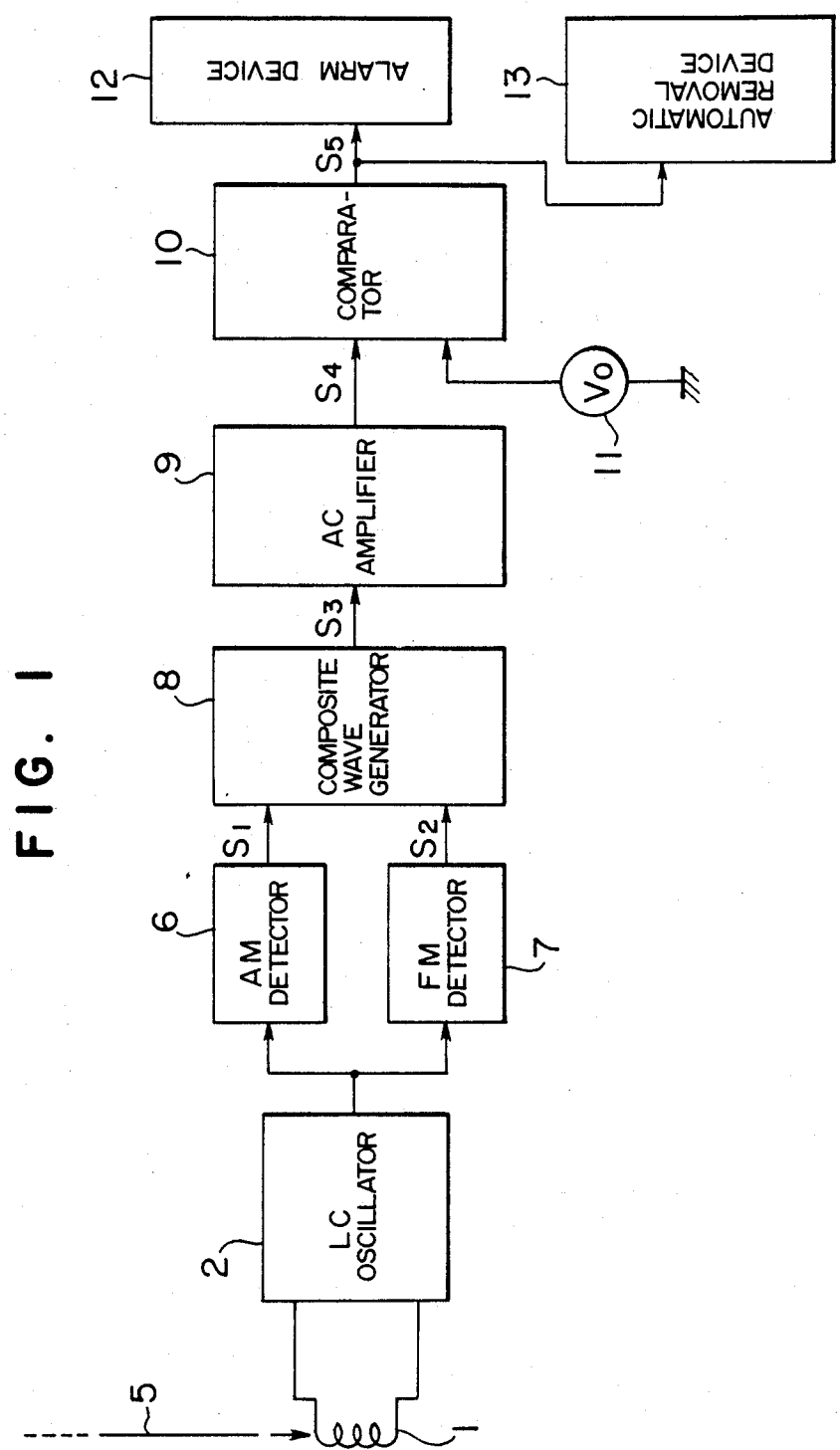
FIG. 1 is a block diagram showing the detection apparatus according to the present invention.
Figure 2:
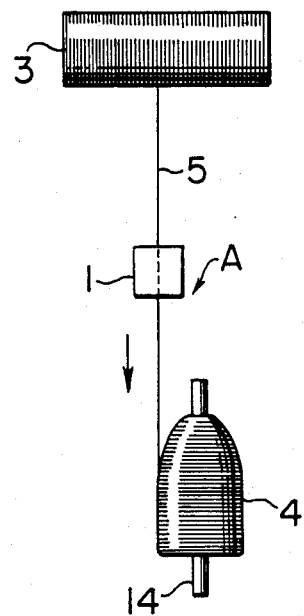
FIG. 2 is a schematic view showing an arrangement of the detection coil in the manufacturing process.

FIG. 1 is a block diagram showing the apparatus for detecting conductive material maldistributed in glass fiber according to the present invention. In FIG. 1, an oscillation coil 1, which is a reactance element, is connected to a loose coupling LC oscillator 2 so that the oscillation coil 1 functions as a circuit component for determining the state of oscillation of the LC oscillator 2. As the LC oscillator 2, a known one may be employed. The frequency of oscillation of the LC oscillator 2 is generally selected to be within a range of from 10 MHz to 50 MHz in which few noises are generally generated, and preferably, a frequency of 30 MHz is used. Further, in the manufacturing process of glass fiber products, the oscillation coil 1 is disposed at a position just below a size applicator at a position (A in FIG. 2 of the drawing) between a cake 3 and a bobbin 4 in the rewinding step, or at a position between a winder and a strand guide. The dimensions of the oscillation coil 1 are selected to be small so as to have a diameter of 3-10 mm and a length of 3-10 mm. The reference numeral 5 represents a part of glass fiber which is in the manufacturing process, the glass fiber being arranged so as to pass through an inner space of the oscillation coil 1 as shown in FIG. 2 or through an external space in the vicinity of the oscillation coil 1. In such an arrangement of the oscillation coil 1 as described above, when a portion of the glass fiber 5 containing maldistributed exceedingly fine conductive material passes through a space in the vicinity of the oscillation coil 1, the reactance (inductance) of the oscillation coil 1 is changed to thereby change the state of oscillation of the LC oscillator 2.

An oscillating current produced from the LC oscillator 2 is supplied to an AM detector 6 and an FM detector 7 which are connected to the output of the LC oscillator 2 in parallel with each other. An AM detection signal $S_1$ taken out by the AM detector 6 and an FM detecting signal $S_2$ taken out by the FM detector 7 are supplied to a composite wave generator 8, in which respective amplitudes of these two signals $S_1$ and $S_2$ are added to each other. The thus obtained composite signal $S_3$ is amplified by an AC amplifier 9 in the next stage. The thus amplified signal $S_4$ is applied to one of the two input terminals of a comparator 10. A reference voltage $V_0$ is applied to the other input terminal of the comparator 10 from a voltage setter 11, so that the signal $S_4$ is compared with the reference voltage $V_0$. On the basis of the result of comparison, it is possible to detect whether target conductive material is contained in the glass fiber 5 or not. The voltage setter 11 is arranged so as to be able to desiredly change the set value of the reference voltage $V_0$. Accordingly, if a desired value of the reference voltage $V_0$ is set as a threshold, it is possible to detect conductive material having a desired length and a desired diameter. That is, when the signal $S_4$ is larger than the reference voltage $V_0$, a detection signal $S_5$ is produced at the output of the comparator 10 so as to prove the detection of conductive material.

Next, description will be made as to the detecting operation of the thus arranged detection apparatus.

Figure 3:
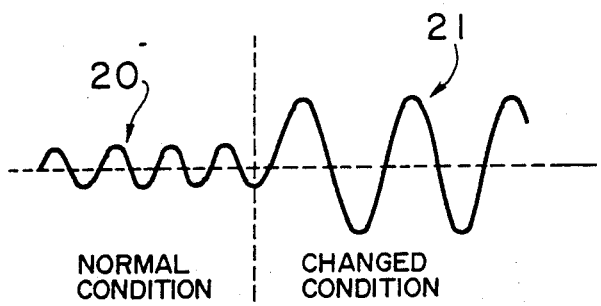
FIG. 3 is a waveform diagram of an output signal of an LC oscillator showing two states of oscillation.

FIG. 3 shows waveforms of the oscillating current produced from the LC oscillator 2 in two states, a waveform 20 being in ;a normal state, a waveform 21 being in a changed state. The waveform 20 in the normal state is generated in the case where the glass fiber 5 is not passing through the inside of or the outside vicinity of the oscillation coil 1, or in the case where no conductive material is contained in the glass fiber 5 even though the glass fiber 5 is actually passing through or by the oscillation coil 1. That is, the waveform 20 is generated in the condition that the inductance of the oscillation coil 1 is not changed but kept in its initial value so that the LC oscillator 2 continues its oscillation in the initially set state. In this case, generally, moisture or size attached on the surface of the glass fiber 5 is being detected. The waveform 21 in the changed state, on the contrary, is generated in the case where glass fiber containing conductive material is passing in the vicinity of the oscillation coil 1. That is, the waveform 21 is generated under the condition that the inductance of the oscillation coil 1 is changed by the existence of the conductive material to thereby change the state of oscillation of the LC oscillator 2. However, when the conductive material is contained in the glass fiber by a very small amount, the change in waveform of the oscillating current is small even though the waveform is changed, and therefore it is difficult to distinguish the waveform of the oscillating current in the changed state from that in the normal state. Thus, the inductance of the oscillation coil 1 is changed in accordance with the existence of conductive material in the glass fiber 5, so that the output signal of the LC oscillator 2 has either one of the waveforms 20 and 21. The waveforms 20 and 21 are different from each other in amplitude as well as in frequency.

Figure 4:
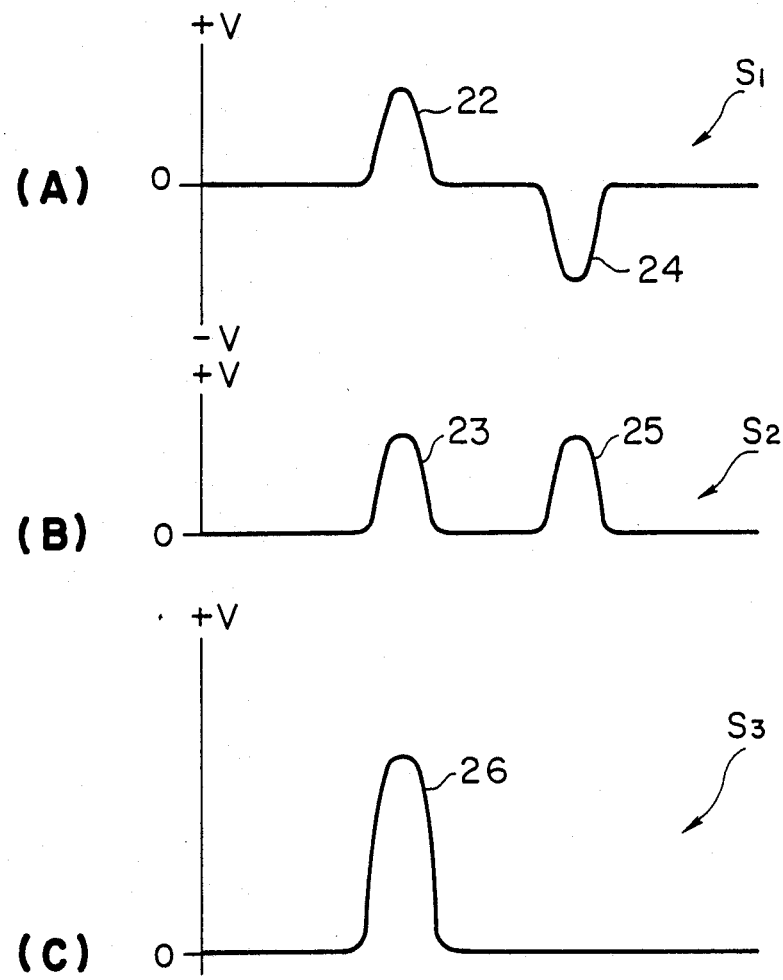
FIG. 4 is a waveform diagram showing states of generation of signals $S_1$, $S_2$, and $S_3$ and relation therebetween.

The output signal of the LC oscillator 2 is branched so as to be supplied to the AM detector 6 and FM detector 7. The AM detector 6 is arranged to detect the oscillation signal in AM manner, and the FM detector 7 is arranged to detect the oscillation signal in FM manner. The diagrams (A) and (B) of FIG. 4 show voltage waveforms of the AM detection signal $S_1$ and the FM detection signal $S_2$ respectively. It is empirically known that the AM detection signal $S_1$ and the FM detection signal $S_2$ have the following features with respect to the changes in waveform. That is, when a portion of the glass fiber 5 containing conductive material passes in the vicinity of the oscillation coil 1, the inductance of the oscillation coil 1 is changed to thereby change the respective waveforms of the signals $S_1$ and $S_2$ towards the positive side (portions 22 and 23 in the drawing). Thereafter, when only a portion of the glass fiber 5 on which moisture or size is attached passes through or by the oscillation coil 1, on the contrary, the inductance of the oscillation coil 1 is changed again to thereby change the respective waveforms of the signals $S_1$ and $S_2$ towards the negative and positive sides respectively (portions 24 and 25 in the drawing). In this case, the AM detection signal $S_1$ and the FM detection signal $S_2$ are adjusted in advance to have the same amplitudes as each other by means of any proper circuit component. As described above, in the case of the FM detection signal $S_2$, conductive material is detected in the same signal state as that in the case of moisture and size, and therefore, the former cannot be distinguished from the latter. In the case of the AM detection signal $S_1$, on the contrary, the waveform is generally inverted between detection of conductive material and detection of moisture or the like, and therefore the former can be clearly distinguished from the latter. However, strictly speaking, even in case of the AM detection signal $S_1$, there is a possibility that in the case of detection of moisture or the like, the waveform is changed towards the positive side by a hunting phenomenon due to an influence of the moisture attached on the surface of the glass fiber 5, and therefore conductive material and moisture or the like cannot be strictly distinguished from each other by use of only the AM detection signal $S_1$.

Therefore, the signals $S_1$ and $S_2$ are supplied to the composite wave generator 8 in the next stage so as to be combined with each other synchronously at a point in time when both the signals $S_1$ and $S_2$ are changed. As a result, in the output signal $S_3$ of the composite wave generator 8, a waveform 26 which is a result of summation of the signals $S_1$ and $S_2$ is generated as shown in the diagram (C) of FIG. 4 when the signals $S_1$ and $S_2$ are in phase (waveforms 22 and 23 respectively) upon detection of conductive material, while substantially no change is generated upon detection of moisture or the like because the signals $S_1$ and $S_2$ are different in phase by 180 degrees (waveforms 24 and 25 respectively) so that the signals $S_1$ and $S_2$ are canceled by each other. Further, in the case of the output signal $S_3$, even if a waveform is generated to a certain extent, the generated waveform can be clearly distinguished from the above-mentioned waveform 26. As described above, the inductance of the oscillation coil 1 is changed in either case of detection of conductive material and detection of only moisture or the like. However, the detection apparatus of this embodiment is arranged such that the change in signal is detected as a change in amplitude as well as in frequency in the AM detection signal $S_1$ and the FM detection signal $S_2$ and both the detection signals $S_1$ and $S_2$ are combined with each other by the composite wave generator 8, so that only the detection of conductive material can be accurately performed with no erroneous recognition.

The thus obtained signal $S_3$ is then amplified by the AC amplifier 9 to a desired level, and the thus amplified signal $S_4$ is applied to the comparator 10 so as to be compared with the reference voltage $V_0$. In the case where the signal $S_4$ is larger than the reference voltage $V_0$, a conductive material detection signal $S_5$ is produced. The signal $S_5$ is further supplied to an alarm device 12 in the next stage so as to inform a worker of detection of conductive material. At the same time, the signal $S_5$ is transferred to an automatic removal apparatus 13 to actuate the latter to cut the glass fiber by a cutter so as to remove a portion of the glass fiber containing the conductive material. Then, the worker connects the cut glass fiber again. It is possible to automatize all the steps of the work described above by using the signal $S_5$.

The coil is used as a reactance element in the foregoing embodiment. The shape of the coil may be desirably modified. Further, in place of the coil, a capacitor having a predetermined shape may be used. Moreover, according to the present invention, conductive material contained in glass fiber can be detected to a minimum diameter is 0.5 μm and a minimum length of 0.5 mm.

In the detection apparatus according to the present invention, particularly, existence of conductive material can be checked with respect to all the portions of glass fiber in every step in the manufacturing process, so that satisfactory detection can be performed.

In the detection apparatus according to the present invention, however, it is not always required that the glass fiber and the reactance element included in the detection apparatus move relative to each other. Even in the case where glass fiber is stationarily disposed in the vicinity of the reactance element, if conductive material is contained in the glass fiber, the detection apparatus according to the present invention can detect the conductive material.

Next, description will be made as to an example to which the detection apparatus according to the present invention is actually applied. As shown in FIG. 2, a cylindrical oscillation coil 1 having a length of 7 mm and an inner diameter of 5 mm was disposed between a cake 3 and a spindle 14 of a rewinder, and glass fiber 5 was caused to run through an inside space of the oscillation coil 1. The oscillation coil 1 is arranged as shown in FIG. 1 so that a change in inductance corresponding to conductive material (mainly, iron sulfide, nickel sulfide, chromium, iron, nickel, copper, or gold) contained in the glass fiber 5 is detected as a change in voltage signal $S_4$. The glass fiber 5 was running, for example, at a speed of 100 m/min. Assuming that a composite wave signal $S_3$ having a voltage value of L [mV] is generated when conductive material having a length of K [mm] is contained the glass fiber 5. This signal $S_3$ was amplified with 94 dB in the AC amplifier 9 and transferred to the comparator 10 in which a reference voltage $V_0$ was so that conductive material having a length of 0.5 mm can be detected. When the signal $S_4$ having a value larger than the voltage value $V_0$ was applied to the comparator 10, the signal $S_5$ was produced from the comparator 10. The automatic removal apparatus 13 was actuated to cut the glass fiber 5 so as to remove a portion of the glass fiber containing conductive material. Then, the operator stopped the spindle 14 and carried out the succeeding processing such as connection of the glass fiber 5, or the like. In this case, arrangement may be made such that a printer or the like is actuated through a relay to record the time when conductive material is detected, the time of working such as cutting, or the like. Data recorded by the printer are utilized for study of working efficiency. The frequency used in the LC oscillator 2 was 30 MHz. The following table shows the results of the experiment.

| Moving speed of Glass fiber | K [mm] | L [mV] |
| --- | --- | --- |
| 100 m/min | 0.5 | 50 |
|  | 1.0 | 100 |
|  | 1.5 | 170 |
|  | 2.0 | 300 |
|  | 3.0 | 500 |
|  | 5.0 | 800 |
|  | 7.0 | 1700 |
|  | 10.0 | 3500 |

As apparent from the foregoing explanation, the detection apparatus according to the present invention is arranged such that a reactance element which is a constituent component of an oscillator set in a predetermined state of oscillation is disposed in a manufacturing process of glass fiber so that conductive material contained in the glass fiber can be detected on the basis of a change in state of oscillation of the oscillator due to a mutual action between the conductive material and the reactance element. Therefore, only the conductive material maldistributed in glass fiber can be detected easily and accurately under the condition that the glass fiber is running, with no influence of moisture or the like attached on the glass fiber. Further, even extremely fine conductive material can be detected. Moreover, it is possible to carry out checking for all the products of glass fiber. Accordingly, there is such an advantage that all the inferior portions of glass fiber can be removed. According to the present invention, it goes without saying that other various effects possibly generated by the arrangement according to the present invention can be obtained.

We claim:

1. A method of detecting conductive material in a glass fiber, which is minute and contained in a very small quantity therein, under the condition that the glass fiber is moved at relatively high speed, the method comprising the steps of providing an oscillator including a reactance element set in an oscillating state which has a predetermined oscillating amplitude value and a predetermined oscillating frequency value existing in a range of a relatively high frequency, moving the glass fiber, which may contain the conductive material to be detected, in the vicinity of the reactance element, detecting instantaneous changes respectively in the oscillating amplitude and oscillating frequency in response to such glass movement, in which the corresponding value is changed from the respective predetermined value to a different value of increasing or decreasing direction relative to the predetermined value, and determining instantaneously the presence of such conductive material upon simultaneously determining that a detected change of the oscillating state is caused by the conductive material contained in the glass fiber, by detecting when the direction of the detected change in the oscillating amplitude and the direction of the simultaneously detected change in oscillating frequency are identical to each other.

2. Method of claim 1 wherein the detection of the instantaneous change in the oscillating amplitude from the predetermined value to a different value is performed by AM detection, and the detection of the instantaneous change in the oscillating frequency from the predetermined value to a different value is performed by FM detection.

3. Method of claim 1 wherein the conductive material to be detected has a length smaller than about 2 mm in the axial direction of the glass fiber.

4. Method of claim 1 wherein the range of the oscillating frequency is 10 to 50 MHz.

5. Method of claim 1 wherein the predetermined oscillating frequency is about 30 MHz.

6. Method of claim 1 wherein the speed of the glass fiber is about 100 m/minute.

7. An apparatus for detecting conductive material in a glass fiber, which is minute and contained in a very small quantity therein, under the condition that the glass fiber is moved at relatively high speed, the apparatus comprising a reactance element disposed for positioning in the vicinity of a moving portion of the glass fiber, an LC oscillator including the reactance element as a circuit component, which is set in an oscillating state which has a predetermined oscillating amplitude value and a predetermined oscillating frequency value existing in a ranged of a relatively high frequency, an AM detector coupled to said oscillator for detecting an instantaneous change from the predetermined value of the oscillating amplitude of the output signal from the LC oscillator, to a different value of increasing or decreasing direction relative to the predetermined value and producing an AM detection signal in response to detection of said instantaneous amplitude change, an FM detector coupled to said oscillator for detecting an instantaneous change from the predetermined value of the oscillating frequency of the output signal from the LC oscillator, to a different value of increasing or decreasing direction relative to the predetermined value and providing an FM detecting signal in response to detection of said instantaneous frequency change, a composite wave generator for summing up the AM and FM detection signals and producing a composite signal, and a comparator for comparing the composite signal with a reference value and producing a conductive material detecting signal when the composite signal is the sum of an oscillating amplitude whose detected change in value and an oscillating frequency whose simultaneously detected change in value are of identical direction.

8. Apparatus of claim 7 wherein the reactance element includes a coil.

9. Apparatus of claim 8 wherein the glass fiber is arranged to pass through an inside space of the coil.

10. Apparatus of claim 8 wherein the coil has such a size that its diameter is about 3 to 10 mm and its length is about 3 to 10 mm.

11. Method of claim 7 wherein the reference value is adjustable to a desired value in relation to a length of the conductive material to be detected.

* * * * *